(12) United States Patent
Flather et al.

(10) Patent No.: US 7,803,438 B2
(45) Date of Patent: Sep. 28, 2010

(54) POLYMERIC SHELL ADHERENTLY SUPPORTED BY A LINER AND A METHOD OF MANUFACTURE

(75) Inventors: Michael Flather, Worcestershire (GB); Paul Saunders, Worcestershire (GB); Dave Narasimhan, Flemington, NJ (US)

(73) Assignee: Ansell Healthcare Products LLC, Red Bank, NJ (US)

( * ) Notice: Subject to any disclaimer, the term of this patent is extended or adjusted under 35 U.S.C. 154(b) by 1435 days.

(21) Appl. No.: 11/210,515

(22) Filed: Aug. 24, 2005

(65) Prior Publication Data

US 2006/0068140 A1 Mar. 30, 2006

Related U.S. Application Data

(60) Provisional application No. 60/614,604, filed on Sep. 30, 2004.

(51) Int. Cl.
 *B29D 22/00* (2006.01)
 *B29D 23/00* (2006.01)
 *B32B 1/08* (2006.01)

(52) U.S. Cl. .................... 428/35.7; 428/35.2; 428/36.6; 428/36.7; 428/423; 428/425.1; 2/161; 2/167; 2/169

(58) Field of Classification Search ...................... 2/161, 2/167, 169; 428/35.2, 35.7, 36.6, 36.7, 423.1, 428/423.9, 425.1
See application file for complete search history.

(56) References Cited

U.S. PATENT DOCUMENTS 2,083,684 A 6/1937 Burke 3,268,647 A 8/1966 Hayes et al.

(Continued)

FOREIGN PATENT DOCUMENTS

DE 29879644 U1 3/2000

(Continued)

OTHER PUBLICATIONS

ISR for PCT/US2005/033457 (Jan. 25, 2006), 2 pgs.

(Continued)

*Primary Examiner*—Michael C Miggins
(74) *Attorney, Agent, or Firm*—Diehl Servilla LLC

(57) ABSTRACT

An article comprising at least one cured, liquid-impervious polymeric shell substantially free from defects, at least one liner, and a non-tacky, thermoplastic adhesive layer between the shell and the liner, wherein the adhesive layer is melted and solidified to create a non-tacky bond between the shell and the liner, which can be moisture-absorbing or cut-resistant, whereby the liner supports and limits stretch ability of the shell, thereby preventing adhesive delamination between the adhesive layer and either of the shell and/or the liner; a method for the manufacture of an article comprising a supported, polymeric shell, such as a glove, a gauntlet, an apron, or a boot, comprising providing a cured, liquid-impervious, polymeric shell, providing a knitted/woven liner, incorporating a non-tacky, thermoplastic adhesive layer between the shell and the liner, such as by hot-melt spraying, dry-powder spraying or fiber-coating, creating intimate contact between the shell, the adhesive layer, and the liner, subjecting the shell, the adhesive layer, and the liner to infrared radiation to melt the adhesive layer and create a bond between the shell and the liner, and cooling the shell; as well as other methods.

18 Claims, 7 Drawing Sheets

U.S. PATENT DOCUMENTS

| | | | |
|---|---|---|---|
| 4,283,244 A | 8/1981 | Hashmi | |
| 4,514,460 A | 4/1985 | Johnson | |
| 4,515,851 A | 5/1985 | Johnson | |
| 4,555,813 A | 12/1985 | Johnson | |
| 4,589,940 A | 5/1986 | Johnson | |
| 4,918,754 A | 4/1990 | Leatherman et al. | |
| 5,070,540 A | 12/1991 | Bettcher et al. | |
| 5,581,812 A | 12/1996 | Krocheski | |
| 5,599,895 A | 2/1997 | Heider | |
| 5,618,904 A | 4/1997 | Martin et al. | |
| 5,700,544 A | 12/1997 | Goodwin et al. | |
| 5,822,791 A | 10/1998 | Baris | |
| 5,932,680 A | 8/1999 | Heider | |
| 6,539,552 B1 | 4/2003 | Yoshida | |
| 6,543,059 B2 | 4/2003 | Szczesuil et al. | |
| 6,596,345 B2 | 7/2003 | Szczesuil et al. | |
| 7,007,308 B1 * | 3/2006 | Howland et al. | 2/161.6 |

FOREIGN PATENT DOCUMENTS

| | | | |
|---|---|---|---|
| FR | 2713048 | | 6/1995 |
| FR | 2713048 | * | 9/1995 |

OTHER PUBLICATIONS

IPRP & Written Opinion, for PCT/US2005/033457 (Mar. 31, 2007), 5 pgs.

* cited by examiner

POLYMERIC SHELL ADHERENTLY SUPPORTED BY A LINER AND A METHOD OF MANUFACTURE

This application claims the benefit of U.S. provisional patent application No. 60/614,604, filed on Sep. 30, 2004.

TECHNICAL FIELD OF THE INVENTION

This invention relates to a polymeric shell, which is supported by an adhesively bonded liner, thereby limiting the stretch of the polymeric shell, and a method of making same.

BACKGROUND OF THE INVENTION

Polymeric shells, including unsupported medical, surgical and other gloves, are typically made of latex. These polymeric shells are produced in an assembly line fashion by dipping a coagulant-coated former of desired shape into an aqueous latex emulsion, thereby gelling the latex and subsequently curing the gelled layer to form the polymeric shell. The aqueous latex emulsion may comprise additives, including viscosity modifiers, waxes, surfactants, stabilizers, cross-linking agents and the like, to produce a cured latex product having specific characteristics, such as thickness, tensile strength, tear and penetration resistance, flexibility; etc., in a controlled manner. Aqueous latexes of different compositions are known in the art, and they include natural rubber latexes, synthetic polyisoprenes, and other synthetic latexes, including neoprene, nitrile compositions, and the like. Typical examples of polymeric shells made from the aqueous dipping process are described in U.S. Pat. No. 3,268,647 to Hayes et al., which discloses the manufacture of rubber gloves.

Polymeric shells with a supported liner are known in the art and are typically used in applications that require a strong latex product commonly used in industrial environments, such as gloves, for protecting hands. A number of patents disclose coating the liner with a latex composition. For example, U.S. Pat. No. 2,083,684 to Burke discloses rubber-coated gloves and a method of making the same. U.S. Pat. Nos. 4,514,460, 4,515,851, 4,555,813, and 4,589,940 to Johnson disclose slip-resistant gloves and a method for their manufacture. U.S. Pat. No. 5,070,540 to Bettcher et al. discloses a protective garment. A metallic wire core and two fiber strand wrappings are coated by dipping in a nitrile rubber composition. U.S. Pat. No. 5,581,812 to Krocheski discloses a leak-proof textile glove. The inner surface of a cut-resistant textile layer is bonded to a leak-proof, petroleum-resistant, polymeric material, such as PVC, without an intervening adhesive layer, since the leak-proof polymeric material is applied to a liner placed on a former. U.S. Pat. No. 5,822,791 to Baris discloses a protective material and a method wherein a cut-resistant, protective layer is coated with an impervious elastomeric material. A typical process for producing these supported gloves includes the use of a liner, which is dressed over a former, optionally treated with a coagulant, and dipped into an aqueous latex emulsion to form a gelled latex layer over the liner, which is then cured. The penetration of the aqueous latex emulsion into the dressed liner results in 'strike-through,' or "penetration," which creates an unsightly appearance of the supported product and makes the article more rigid and less flexible. A number of steps are taken to minimize 'strike-through,' including coagulant coating of the liner as a blocking agent, and increasing the viscosity of the aqueous latex emulsion to prevent the penetration of the aqueous emulsion into the liner; etc. The aqueous latex emulsion used may comprise several additives, such as stabilizers, foaming agents, cross-linking agents, waxes, and surfactants. The latex composition may be natural rubber, polyisoprene, neoprene, or nitrile rubber; etc. These supported polymeric shell products provide sufficient protection to the hands of the wearer. The dipping and drying of a glove former in a latex emulsion to form a glove is disclosed. However, the chemical resistance of the polymeric shell is generally inadequate due to poor coverage of the latex emulsion over the liner and may have holes in the latex layer where the fibers of the liner cross. A further and perhaps more serious consequence of coating over a knitted fabric is the possibility that the resultant polymeric film is compromised, resulting in a non-uniform thickness, which may compromise the chemical-resistant barrier of the film in parts or which may not be liquid-proof. This is due to the potential of surface fibers passing into or through the coating, hence providing an easier path for liquids to pass or permeate through the polymeric film. Foamed latex layers may have interconnected porosity, which also may provide decreased chemical resistance to the supported polymeric shell latex article.

U.S. Pat. No. 4,283,244 to Hashmi discloses a method of making fabric-lined articles. This method of making a lined elastomeric article comprises the steps of applying a coating of adhesive in a liquid state to an elastomeric article on a form, drying the adhesive on the article to form a pressure-sensitive adhesive coating, treating the adhesive coating with a lubricant, and thereafter applying a preformed lining over the article and the adhesive coating to connect adhesively the lining to the elastomeric article. The elastomeric article is a latex product produced by dipping a coagulant-treated former into an aqueous latex emulsion and drying and curing the elastomeric article on the former. The adhesive is 68096-01 resin supplied by Evans Adhesives of Columbus, Ohio, suspended in water. The elastomeric article on the former is dipped in the adhesive, dried to form a pressure-sensitive adhesive coating, lubricated, and dressed with a liner. The lined elastomeric article is removed from the former and turned inside-out. Unfortunately, the sweating action combined with body temperature results in the extraction or dissolution of the adhesive, producing an unpleasant skin feel. The adhesive also is soft, has low strength properties, and stays tacky even after drying.

U.S. Pat. No. 4,918,754 to Leatherman et al. discloses a flocked glove and a plastic sleeve member bonded thereto. A preformed, flock-lined, rubber-like glove has its cuff folded back to expose the flocked lining, is mounted in a rotating support, and is sprayed with a hot-melt adhesive on the flock-lined, folded cuff. The glove is telescoped onto a polyethylene sleeve, and the adhesive is melted by high frequency heating to bond the polyethylene sleeve with the cuff. The adhesive bonds the polyethylene sleeve to the cuff portion of the glove and does not bond the entire polymeric shell with a liner.

U.S. Pat. Nos. 5,599,895, 5,618,904, and 5,932,680 disclose moisture-curing polyurethane hot-melt adhesive. The hot-melt adhesive includes at least one polyurethane prepolymer of at least one polyisocyanate, toluene diisocyanate, and/or MDI, at least one polyalkylene glycol, at least one polyester glycol, and optional additives, such as a stabilizer, particularly toluenesulfonyl isocyanate.

U.S. Pat. Nos. 6,543,059 and 6,596,345 to Szczesuil et al. disclose a protective glove and a method for making same. This protective glove for a human hand includes an inner glove of polyester, non-woven, needle-punched material and a melt-sprayed polyurethane coating. This non-woven needle punched material has no mechanical integrity, unlike a woven or knitted fabric, and the hot-melt-sprayed polyurethane adhesive holds the configuration together, forming a glove.

The melt-sprayed glove is heated to a temperature of 300 to 325° F. to allow the remelted polyurethane to penetrate the inner glove to a depth short of penetrating to the inner surface of the inner glove. The polyurethane coating on the outer surface of the inner glove cures in approximately 24 hours by reaction with ambient moisture. The inner glove is further coated with a rubberized material to produce an inner glove held together by the rubber, which is then cut into pieces and sewn to form a glove with internal sewn seams. Such a glove is not liquid-impervious, since these sewn seams are not bonded and leak and, therefore, not chemically resistant. The protective glove is said to protect from puncture.

U.S. Pat. No. 6,539,552 to Yoshida discloses a flexible waterproof glove. This waterproof glove is formed of a flexible inner glove body of a base fabric that is thermally bonded with a low-melting, thermal plastic resin film and a flexible outer glove body of the same fabric. The thermal bonding of the inner glove with the outer glove is accomplished by heating the glove to melt the low-melting, thermal plastic resin film, which has a lower melting point than that of the base fabric. The melted thermal plastic resin film results in a watertight glove. In one embodiment, the thumb portion of the glove is manufactured separately and bonded to the rest of the glove to provide improved thumb movement. The molten and solidified polymer thermally bonded to the inner and outer glove body results in a watertight glove. The overall rigidity and resistance to movement of the glove is addressed by the separate attachment of the thumb component to the glove. There is no latex or polymeric shell in this glove. Thus, this glove has no stretch characteristics resembling those that are commonly available in a latex-based glove product.

Therefore, there is a strong need in the art for a supported, chemically resistant, polymeric shell, latex article that effectively manages moisture, such as sweat, and exposure to body temperature. The liner provides stretch resistance, a comfortable feel, moisture (e.g., sweat) management, and cut-resistance as desired, while the polymeric shell provides chemical resistance. There is also a need in the art for a manufacturing process that produces a supported, polymeric shell, latex article in a production environment. A more efficient method for adhering a liner to a polymeric shell is needed. Additionally, a method is needed that substantially minimizes, and preferably eliminates, strike-through, i.e., penetration of a latex composition into the liner. Further, a method is needed that will insure the physical integrity of the polymeric shell, i.e., no thin or weak areas or holes, thus providing a sound liquid-proof barrier. It is an object of the present invention to provide such a method. It is another object of the present invention to provide an article comprising a polymeric shell, an adhesive, and a liner, and having physical integrity taking advantage of the unique properties of the liner and that of a chemically resistant liquid-proof polymeric shell. These and other objects and advantages, as well as additional inventive features, will be apparent from the detailed description provided herein.

BRIEF SUMMARY OF THE INVENTION

The present invention provides an article comprising at least one cured, liquid-impervious polymeric shell substantially free from defects; at least one liner; and a non-tacky, thermoplastic adhesive layer placed between the at least one shell and the at least one liner. The adhesive layer is applied to either the liner or the polymeric shell, melted and solidified to create a non-tacky bond between the at least one shell and the at least one liner. The liner supports and limits stretch ability of the shell, thereby preventing adhesive delamination from either the shell and/or the liner.

The present invention further provides a method for the manufacture of an article comprising a supported, polymeric shell. The method comprises providing a cured, liquid-impervious, polymeric shell produced by dipping a coagulant-coated former into an aqueous latex emulsion, gelling a latex layer on the former, and heating the gelled latex layer on the former to crosslink and cure the latex layer. The method further comprises providing a liner knitted or woven using fibers selected from the group consisting of cotton, rayon, polyester, polypropylene, Kevlar™, Spectra™, steel wire, or a combination thereof, placing the polymeric shell over a skeletal support, coating the external surface of the polymeric shell with a non-tacky, thermoplastic adhesive layer, dressing the shell with the liner such that the adhesive layer is between the polymeric shell and the liner; inflating the polymeric shell with air pressure to create intimate contact between the polymeric shell, the adhesive layer, and the liner, subjecting the polymeric shell with the adhesive layer and the dressed liner to infrared radiation, thereby melting the adhesive layer and creating a bond between the polymeric shell and the liner, and cooling the polymeric shell with the adhesive layer and the liner to create the supported, polymeric shell article.

Another method of manufacture is also provided. The method comprises providing a cured, liquid-impervious, polymeric shell produced as described above, providing a liner knitted or woven as described above, placing the liner over a former, coating the external surface of the liner with a non-tacky, thermoplastic adhesive layer, stripping the adhesive layer-coated liner from the former, placing the polymeric shell over a skeletal support, dressing the polymeric shell with the adhesive layer-coated liner in such a manner that the adhesive layer is between the shell and the liner, and inflating the polymeric shell, subjecting the shell to infrared radiation, and cooling the shell as described above.

Yet another method of manufacture is provided. The method comprises providing a liquid-impervious polymeric shell produced as described above, coating fibers with a non-tacky, thermoplastic adhesive, providing a liner knitted or woven using the fibers coated with adhesive, placing the polymeric shell over a skeletal support, dressing the polymeric shell with the liner, and inflating the polymeric shell, subjecting the shell to infrared radiation, and cooling the shell as described above.

Still yet another method of manufacture is provided. The method comprises providing first and second liquid-impervious polymeric shells produced as described above, stripping the first and second polymeric shells from the formers, placing the first polymeric shell over a skeletal support, coating the external surface of the first polymeric shell with a first non-tacky, thermoplastic adhesive layer, providing a cut-resistant liner knitted or woven using fibers such as Kevlar™, Spectra™ or steel wire as described above, dressing the first polymeric shell with the cut-resistant liner such that the adhesive layer is between the polymeric shell and the liner, coating the external surface of the cut-resistant liner with a second non-tacky thermoplastic adhesive layer, dressing the first shell with the adhesive layer-coated liner with the second shell, and inflating the shell, subjecting the shells to infrared radiation, and cooling the shells as described above.

Even still yet another method of manufacture is provided. The method comprises providing first and second liquid-impervious polymeric shells produced as described above, stripping the first and second polymeric shells from the formers, providing a cut-resistant liner knitted or woven using fibers as described above, applying a thermoplastic adhesive to the inner and outer surfaces of the liner by hot-melt or dry-powder spraying, placing the first shell over a skeletal support, dressing the first polymeric shell with the adhesive-coated liner, dressing the first polymeric shell with the adhesive-coated liner with the second polymeric shell, and inflating the polymeric shells, subjecting the shells to infrared radiation, and cooling the polymeric shells as described above.

DETAILED DESCRIPTION OF THE INVENTION

Figure 1A:
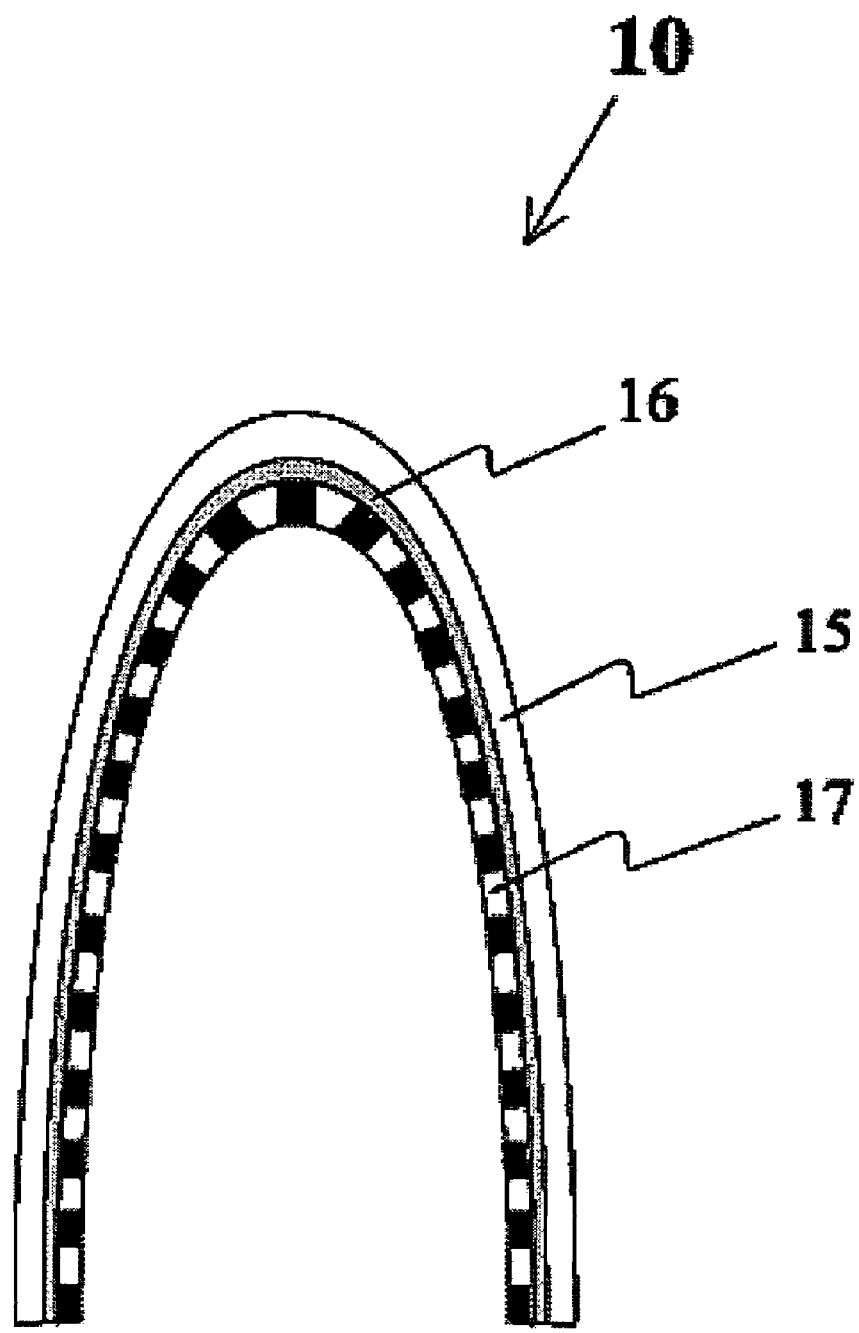
FIG. 1A illustrates a fragmentary cross-sectional view of a polymeric shell latex article supported by a liner that is bonded on the inside of the polymeric shell by an adhesive layer in accordance with the present invention.

The present invention provides an article comprising at least one cured, liquid-impervious polymeric shell substantially free from defects, at least one liner, and a non-tacky, thermoplastic adhesive layer placed between the at least one polymeric shell and the at least one liner. The adhesive layer is melted and solidified to create a non-tacky bond between the at least one polymeric shell and the at least one liner. The liner supports the shell and limits stretch ability of the polymeric shell to that of the liner, thereby limiting stress at the polymeric shell-adhesive layer interface and at the adhesive layer-liner interface and preventing adhesive delamination at the interfaces. The adhesive layer is immune to leaching or extraction by moisture or sweat at body temperature.

The polymeric shell needs to be liquid-impermeable so that the resultant article is chemically resistant. The polymeric shell can comprise natural and/or synthetic latex, such as nitrile latex, styrene butadiene rubber (SBR), and other standard latex variants. The polymeric shell typically stretches from about 50-500%, whereas a woven textile liner stretches, depending on fiber geometry, from about 0.5-5%, and a knitted liner stretches from about 5-20%.

The polymeric shell can be prepared by any suitable method, including evaporation of a thin layer of polymer dissolved in a solvent or gelation of an aqueous latex emulsion over a coagulant-coated former. Gelation over a coagulant-coated former is preferred. In the preferred method an aqueous latex composition of natural latex or a synthetic latex composition comprising polyisoprene, nitrile, neoprene, and the like, is gelled and later cured on a coagulant-coated former to produce a liquid-impervious polymeric shell. The most commonly employed method of manufacturing the polymeric shell is to dip a coagulant-coated former in the shape of the desired article in an aqueous latex emulsion to gel a latex layer over the formed surface and to heat the gelled latex to a temperature that cross-links and cures the latex layer. Since the gelled latex layer is produced over the smooth surface of the former with no liner there between, a substantially defect-free liquid impervious polymeric shell is produced.

The liner can comprise a woven textile fabric or a knitted textile fabric. The liner can comprise cotton, rayon, polyester, polypropylene, Kevlar™ (DuPont, Wilmington, Del.), Spectra™ (Honeywell, Morristown, N.J.), steel wire, or any combination of two or more of the foregoing. A liner comprising cotton and/or rayon, for example, can be placed on the skin-contacting surface of the article, thereby providing a comfortable feel and moisture-absorption. A liner comprising steel wire, Kevlar™, and/or Spectra™, can be placed on the exterior surface of the article or between two polymeric shell layers of an article, thereby providing cut-resistance. Such liners can be used in combination.

There are several key characteristics needed for the adhesive layer to create a satisfactory bond between the polymeric shell and the liner. First, the adhesive composition must be non-tacky so that the liner or shell can be dressed one over the other. Second, the adhesive composition must be a thermoplastic polymer, which melts readily at a temperature that is sufficiently low so that it can be re-melted during the bonding process without damaging the shell or the liner. On the other hand, the thermoplastic polymer must melt at a temperature that is sufficiently high so that it is not affected by body temperature or the temperature of conditions of use. In addition, the adhesive layer preferably resists moisture and sweat so that the adhesive layer is not extracted and the skin is not irritated. Any polymer that is non-tacky at ambient temperature but can be melted at a temperature that does not degrade the shell or the liner can be used. The adhesive layer can comprise a polymer selected from the group consisting of low molecular weight polyethylene, polyester, ethyl vinyl acetate, ethylene 2-ethyl hexyl acrylate polymer, and polyurethane, and has a melting point of less than about 140° C. Polyurethane is preferred. The adhesive may contain a thermosetting component, which allows the adhesive to harden due to reactions therein. An example of a suitable adhesive is polyurethane with isocyanate, such as grade 35-503, which is available from Sovereign Specialty Chemicals (Chicago, Ill.), or 3M Jet-weld™ (St. Paul, Minn.), which causes cross-linking of the adhesive upon exposure to moisture. The strength of the bond increases as a function of time of exposure to moisture, until all of the cross-linking agent is exhausted. The adhesive is preferably applied in an amount in the range of about 0.001-0.01 g/cm$^2$.

The polymeric shell, the liner, and the adhesive layer have different stretching characteristics. When a fixed load is applied to a material, the applied stress level is the applied load divided by the cross-sectional area. The material has a strain, which is the applied stress divided by the modulus of elasticity of the material, providing the stretch ability of the material for the simple stress state of pure tension. When the polymeric shell, adhesive layer, and liner are joined together and a load is applied, the strain in all of these three elements is equal, unless they separate at their interfaces. Because the least stretchable member primarily carries the load, the most stretchable member is supported from stretching. In the context of the present invention, the polymeric shell is most stretchable and is supported by the liner, which is the least stretchable element. The adhesive layer serves to transfer the load from the polymeric shell to the liner. There are two methods by which the polymeric shell is supported by the liner. In the first method, the stretch ability of the adhesive layer is less than that of the polymeric shell but greater than that of the supporting liner. In this case, the polymeric shell and the supporting liner are intimately bonded to the adhesive layer, and the overall stretch of the supported polymeric shell is closer to that of the stretch ability of the supporting liner. In the second method, the adhesive layer has a stretch ability closer to that of the polymeric shell, and the penetration of the adhesive into the interstices of the knitted or woven fabric is relied on to transfer the load to the supporting liner from the polymeric shell.

Typical polymeric shells stretch from about 50-500%, whereas the liner stretches from about 0.5-20%, depending on how the fibers are packed. For example, if the liner is woven, stretch ability is limited by the size of the fiber used and the spacing between the fibers. When the woven liner is stretched, it can only stretch until the fibers contact each other. A woven liner with tight fiber packing has a very limited stretch ability, which may be in the range of about 0.5-5%. A knitted liner, on the other hand, is more stretchable and can stretch from about 5-20%. The adhesive layer generally has different mechanical characteristics from those of the shell or the liner. If the adhesive layer has low stretch ability and is applied only to the polymeric shell, the stretching of the polymeric shell will result in delamination at the polymeric shell-adhesive layer interface. This is due to the higher modulus of elasticity and reduced stretch ability of the adhesive layer, which may stretch about 10-100% as compared to the polymeric shell, which typically stretches about 50-500%. The only way to prevent the delamination or physical separation of the polymeric shell from the adhesive layer is to prevent the stretching of the polymeric shell. This is successfully accomplished by bonding the side of the adhesive layer, which is opposed to the side of the adhesive layer bonding to the polymeric shell, to a liner having sufficient mechanical integrity. The resulting composite does not stretch very much, i.e., more like the liner than the shell. When the adhesive layer stretches about 100-600%, such as when the adhesive is moisture-curing polyurethane, no delamination occurs at the polymeric shell-adhesive layer interface. In this case, successful load transfer to the liner is achieved by allowing the adhesive to penetrate the spaces between the fibers in the knitted/woven liner, thereby causing peg-like bonding. Depending on composition and the method employed to coat the adhesive layer to a substrate, i.e., shell or liner, the adhesive layer stretches from about 10-600%. Preferably, the method employed to coat the adhesive layer to the substrate ensures load transfer from the shell to the liner by the adhesive layer. When the adhesive layer stretches from about 100-600%, the adhesive needs to penetrate between the knitted/woven fibers of the liner to a provide a peg-like bond. When the adhesive layer stretches from about 10-100%, penetration of the adhesive layer into the liner is not necessary.

A number of thermoplastic adhesive systems are available that stretch from about 10-100%. These include low molecular weight polyethylene (mp=110° C.), polyester (mp=120° C.), ethylene vinyl acetate (mp=121° C.), ethylene 2-ethyl hexyl acrylate polymer, EEHA (mp=125° C.), and thermoplastic polyurethane, such as RTP-2300A (mp=111° C.) from RTP Co., Winona, Minn. These polymers can be sprayed as a molten liquid and solidify as a non-tacky layer suitable for use in the context of the present invention.

Alternatively, the adhesive layer can comprise a moisture-cured, cross-linking polyurethane, which can be sprayed as a liquid and which stretches from about 500-600%, and does not separate from the polymeric shell. For example, 3M Jet-weld™ can be sprayed at 121° C. as a jet and cures and cross-links by reaction with moisture. Another example is polyurethane with isocyanate, such as grade 35-503, which is available from Sovereign Specialty Chemicals. When a polymeric shell is adhered to a liner with a moisture-cured, thermoplastic polyurethane adhesive, the liner breaks to pieces without separation at the shell-adhesive layer interface or at the adhesive-liner interface indicating complete load transfer to the liner to such an extent that complete disintegration of the liner results. Thus, a moisture-cured, thermoplastic polyurethane adhesive is preferred.

Since the polymeric shell is made from a standard conventional dipping, gelation, and curing process, it can be produced at the same location in a continuous process production line or removed from storage just prior to the liner/adhesive bonding operation. As a matter of fact, the physical location of the polymeric shell manufacturing plant can be separated from the liner adhesive bonding process facility. Due to this spatial and temporal capability, the production process for a supported polymeric shell product can be "just in time" according to orders received, thereby providing improved cost structure.

The polymeric shell can be coated with the non-tacky adhesive layer and bonded to a liner. In this case, the polymeric shell is placed over a former, coated with the non-tacky thermoplastic adhesive layer, and cooled to ambient temperature. Then, a liner is dressed over the adhesive layer-coated polymeric shell and heated to melt the adhesive layer. When the polymeric shell is removed from the former and inverted, the liner is on the interior surface of the polymeric shell. In a preferred embodiment, the polymeric shell can be supported by a skeletal shell, coated with a non-tacky adhesive layer, and dressed with a liner. The polymeric shell supported by the skeletal former is inflated to allow intimate contact between the polymeric shell and the liner and subjected to infrared heat to melt the adhesive layer. The polymeric article is inverted so that the liner is inside the polymeric shell. The liner, again, limits the stretch ability of the polymeric shell.

Accordingly, in view of the above, the method can comprise the steps of:
a) providing a cured, liquid-impervious, polymeric shell produced by dipping a coagulant-coated former into an aqueous latex emulsion, gelling a latex layer on the former, and heating the gelled latex layer on the former to crosslink and cure the latex layer;
b) providing a liner knitted or woven using fibers selected from the group consisting of cotton, rayon, polyester, polypropylene, Kevlar™, Spectra™, steel wire, or a combination thereof;
c) placing the shell over a skeletal support;
d) coating the external surface of the shell on the skeletal support with a non-tacky, thermoplastic adhesive layer;
e) dressing the shell with the liner such that the adhesive layer is between the shell and the liner;
f) inflating the shell placed over the skeletal support with air pressure to create intimate contact between the polymeric shell, the adhesive layer, and the liner;
g) subjecting the shell with the adhesive layer and the dressed liner to infrared radiation, thereby melting the adhesive layer and creating a bond between the shell and the liner; and h) cooling the shell with the adhesive layer and the liner to create the supported, polymeric shell. The liner can comprise cotton, rayon, or a combination thereof such that, when the shell is inverted, a moisture-absorbing article is produced. Alternatively, the liner can comprise Kevlar™, Spectra™, steel wire, or a combination thereof, such that the shell produces a cut-resistant article. The adhesive layer can be coated on the external surface of the shell on the skeletal support by hot-melt spraying or dry-powder spraying.

Alternatively, the liner can be coated with the non-tacky adhesive layer and bonded to a polymeric shell. In this case, the polymeric shell is placed over a former, and the liner is coated with the non-tacky thermoplastic adhesive layer. The adhesive layer-coated liner is dressed over the polymeric shell and heated to melt the adhesive layer. The liner is then bonded to the exterior of the polymeric shell. In a preferred embodiment, the polymeric shell is supported by a skeletal shell and dressed with an adhesive layer-coated liner, such that the adhesive layer is between the polymeric shell and the liner. The assembly is then heated to melt the adhesive layer, thereby creating a bond between the polymeric shell and the liner.

Accordingly, in view of the above, the method can comprise the steps of:

a) providing a cured, liquid-impervious, polymeric shell produced by dipping a coagulant-coated former into an aqueous latex emulsion, gelling a latex layer on the former, and heating the gelled latex layer on the former to crosslink and cure the latex layer;
b) providing a liner knitted or woven using fibers selected from cotton, rayon, polyester, polypropylene, Kevlar™, Spectra™, steel wire, or a combination thereof;
c) placing the liner over a former;
d) coating the external surface of the liner on the former with a non-tacky, thermoplastic adhesive layer;
e) stripping the adhesive layer-coated liner from the former;
f) placing the shell over a skeletal support;
g) dressing the shell with the adhesive layer-coated liner in such a manner that the adhesive layer is between the shell and the liner;
h) inflating the shell placed over the skeletal support with air pressure to create intimate contact between the polymeric shell, the adhesive layer, and the liner;
i) subjecting the shell with the adhesive layer and the liner to infrared radiation, thereby melting the adhesive layer and creating a bond between the shell and the liner; and
j) cooling the shell with the adhesive layer and the liner to create the supported, polymeric shell article. The liner can comprise cotton, rayon, polyester, polypropylene, or a combination thereof such that, when the supported polymeric shell is inverted, a moisture-absorbing article is produced. Alternatively, the liner can comprise Kevlar™, Spectra™, steel wire, or a combination thereof, such that the supported polymeric shell produces a cut-resistant article. The adhesive layer can be coated on the external surface of the liner on the former by hot-melt spraying or dry-powder spraying.

Alternatively, the fibers used to knit or weave the liner can be coated with the non-tacky thermoplastic adhesive prior to weaving or knitting. In this embodiment, the method can comprise the steps of:

a) providing a cured, liquid-impervious polymeric shell produced by dipping a coagulant-coated former into an aqueous latex emulsion, gelling a latex layer on the former, and heating the gelled latex layer on the former to crosslink and cure the latex layer;
b) coating fibers selected from cotton, rayon, polyester, polypropylene, Kevlar™, Spectra™, steel wire, or a combination thereof with a non-tacky, thermoplastic adhesive;
c) providing a liner knitted or woven liner using the fibers coated with adhesive;
d) placing the shell over a skeletal support;
e) dressing the shell with the liner;
f) inflating the shell placed over the skeletal support with air pressure to create intimate contact between the liner, the thermoplastic adhesive, and the shell;
g) subjecting the shell, the liner, and the thermoplastic adhesive to infrared radiation, thereby melting the adhesive and creating a bond between the shell and the liner; and
h) cooling the shell with the adhesive and the liner to create the supported, polymeric shell article. The liner can comprise cotton, rayon, or a combination thereof such that, when the shell is inverted, a moisture-absorbing article is produced. Alternatively, the liner can comprise Kevlar™, Spectra™, steel wire, or a combination thereof such that the shell produces a cut-resistant article.

In yet another embodiment, the method can comprise the steps of:

a) providing first and second cured, liquid-impervious polymeric shells by separately dipping two coagulant-coated formers into an aqueous latex emulsion, gelling a latex layer on each of the two formers, heating the gelled latex layers on the formers to crosslink and cure the latex layers, and stripping the cured first and second polymeric shells from the formers;
b) placing the first polymeric shell over a skeletal support;
c) coating the external surface of the first polymeric shell on the skeletal former with a first non-tacky, thermoplastic adhesive layer;
d) providing a cut-resistant liner knitted or woven using fibers selected from Kevlar™, Spectra™, steel wire, or a combination thereof;
e) dressing the first polymeric shell with the adhesive layer-coated cut-resistant liner such that the adhesive layer is between the first shell and the liner;
f) coating the external surface of the cut-resistant liner with a second non-tacky thermoplastic adhesive layer;
g) dressing first shell with the adhesive layer-coated liner, with the second shell;
h) inflating the first shell placed over the skeletal support with air pressure to create intimate contact between the first shell, the first adhesive layer, the cut-resistant liner, the second adhesive layer and the second shell;
i) subjecting the first shell, the first adhesive layer, the cut-resistant liner, the second adhesive layer, and the second shell to infrared radiation, thereby melting the adhesive layer and creating a bond between the first shell, the cut-resistant liner, and the second shell;
j) cooling the shells bonded with adhesive layers to create the cut-resistant, supported polymeric shell article; and
k) optionally coating the external surface of the cut-resistant liner with a flexible polymeric layer.

In still yet another embodiment, the method can comprise the steps of:

a) providing first and second cured, liquid-impervious polymeric shells by separately dipping two coagulant-coated formers into an aqueous latex emulsion, gelling a latex layer on each of the two formers, heating the gelled latex layers on the formers to crosslink and cure the latex layers, and stripping the cured first and second polymeric shells from the formers;

b) providing a cut-resistant liner knitted or woven using fibers selected from Kevlar™, Spectra™, steel wire, or a combination thereof;

c) applying a thermoplastic adhesive, which is solid and non-tacky at ambient temperature and which comprises a polyurethane thermoplastic adhesive, to the inner and outer surfaces of a cut-resistant liner by hot-melt spraying or dry-powder spraying;

d) placing the first shell over a skeletal support;

e) dressing the first shell with the adhesive coated liner;

f) dressing the first shell with the adhesive-coated liner with the second shell;

g) inflating the first shell placed over the skeletal support with air pressure to create intimate contact between the first shell, the adhesive-coated liner, and the second shell;

h) subjecting the first shell, the adhesive-coated liner, and the second shell to infrared radiation, thereby melting the adhesive and creating a bond between the first shell, the cut-resistant liner, and the second shell;

i) cooling the shells bonded with adhesive layers to create the cut-resistant, supported polymeric shell article; and j) optionally coating the external surface of the cut-resistant liner with a flexible polymeric layer.

In the context of the above methods, hot-melt spraying can comprise the steps of melting the adhesive, delivering the adhesive to a nozzle, which sprays the hot-melt adhesive on either of the polymeric shell or the liner. The spray pattern can be selected to provide optimal coverage of the shell or liner. Typically, the adhesive used is small, e.g., about 0.001-0.01 g/cm$^2$ or approximately 0.5-5 g per pair of gloves, thereby creating a thin adhesive layer suited for bonding. This small quantity of hot-melt adhesive applied stays nearly at the same place where it was applied during the melting and bonding process, rather than running down complex three-dimensional surfaces of the polymeric shell. Therefore, it is important that the quantity of adhesive used is limited so as to prevent formation of non-flexible regions in the supported polymeric shell article. The adhesive layer is then cooled to ambient temperature, at which time the adhesive layer is substantially non-tacky. This non-tacky property is important for dressing the adhesive-coated component (i.e., shell or liner) with the non-adhesive-coated component (i.e., liner or shell). A sticky adhesive will prevent the proper dressing of the adhesive-coated component.

Dry-powder spraying in the context of the above methods can comprise applying the adhesive as a dry powder at ambient temperature, at which time the adhesive is substantially non-tacky. The adhesive-coated component can then be easily dressed with the non-adhesive-coated component.

When the article is a glove, a convenient method of bonding an adhesive-coated polymeric shell shaped as a glove is to apply the glove to a skeleton form, which has metallic rods of small diameter that act as holders for fingers of the glove. The wrist extension of the glove is inserted over a conical section directly below the rod finger supports and clamped so as to make the glove airtight. The liner is slipped over the non-sticky adhesive-coated polymeric glove shell. Compressed air is pumped inside the glove, and the glove polymeric shell with the adhesive coating is inflated until it contacts and is restrained by the liner. In this condition, the liner is in contact with the adhesive-coated polymeric shell practically everywhere. The inflated glove assembly is moved to a heating station, which subjects the assembly to a temperature sufficient to melt the adhesive, i.e., making the adhesive tacky. An infrared heat source or a convection heat source can be used in the heating station. The assembly is cooled to ambient temperature, at which time the adhesive is securely bonded to the liner and the polymeric shell, is non-tacky, and cannot be leached by sweat or degraded by body temperature.

Referring to FIG. 1A, there is shown a fragmentary portion of a supported polymeric shell 10, i.e., a finger portion of a moisture-absorbing glove, comprising a polymeric shell 15, a liner 17, and an adhesive layer 16. During processing, the polymeric shell is turned inside-out with the adhesive layer over the outer surface. The liner is slipped over the non-tacky adhesive layer and heated to melt the adhesive layer, thereby creating the bond between the polymeric shell and the liner. The bond between the polymeric shell, the adhesive layer, and the liner prevents the excessive stretching of the polymeric shell and, therefore, delamination at the interface between the polymeric shell and the adhesive layer.

Figure 1B:
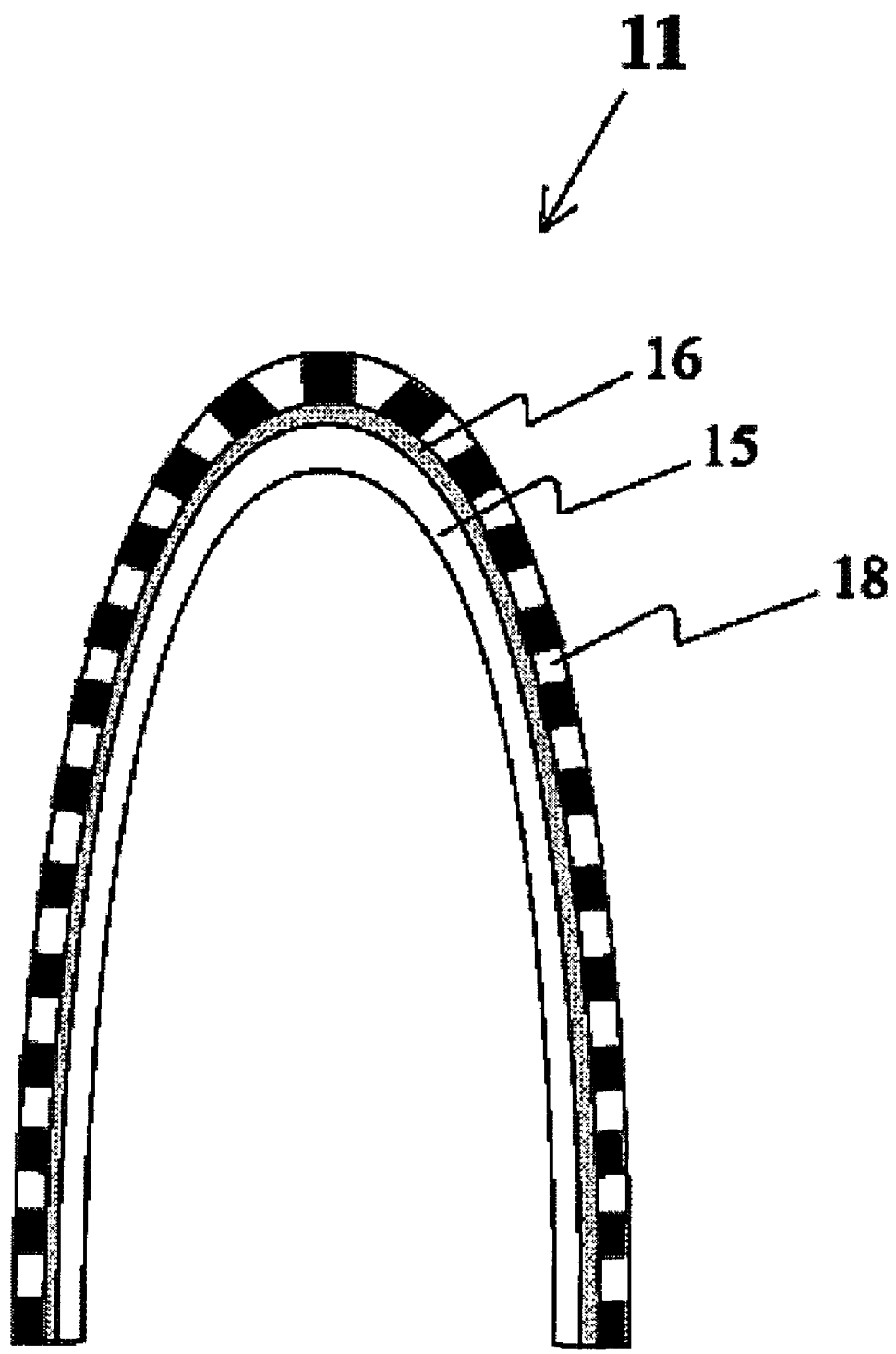
FIG. 1B illustrates a fragmentary cross-sectional view of a polymeric shell latex article supported by a cut-resistant liner that is bonded on the outside of the polymeric shell with an adhesive layer in accordance with the present invention.

Referring to FIG. 1B, there is shown a fragmentary portion of a supported polymeric shell 11, i.e., a finger portion of a cut-resistant glove, comprising a polymeric shell 15, a cut-resistant liner 18, and an adhesive layer 16. During processing, the polymeric shell is turned inside-out with the adhesive layer over the outer surface. The cut-resistant liner is slipped over the non-tacky adhesive layer and heated to melt the adhesive layer, thereby creating a bond between the polymeric shell and the liner. As described above for the moisture-absorbing glove, the bond between the polymeric shell, the adhesive layer, and the liner prevents the excessive stretching of the polymeric shell and, therefore, delamination at the interface between the polymeric shell and the adhesive layer. In practice, after the bond between the cut-resistant liner and the polymeric shell is achieved, the external surface of the cut-resistant liner can be coated with a protective, flexible, polymeric layer, such as polyurethane latex, so as to provide improved product appearance and to protect the cut-resistant fibers from damage.

Figure 1C:
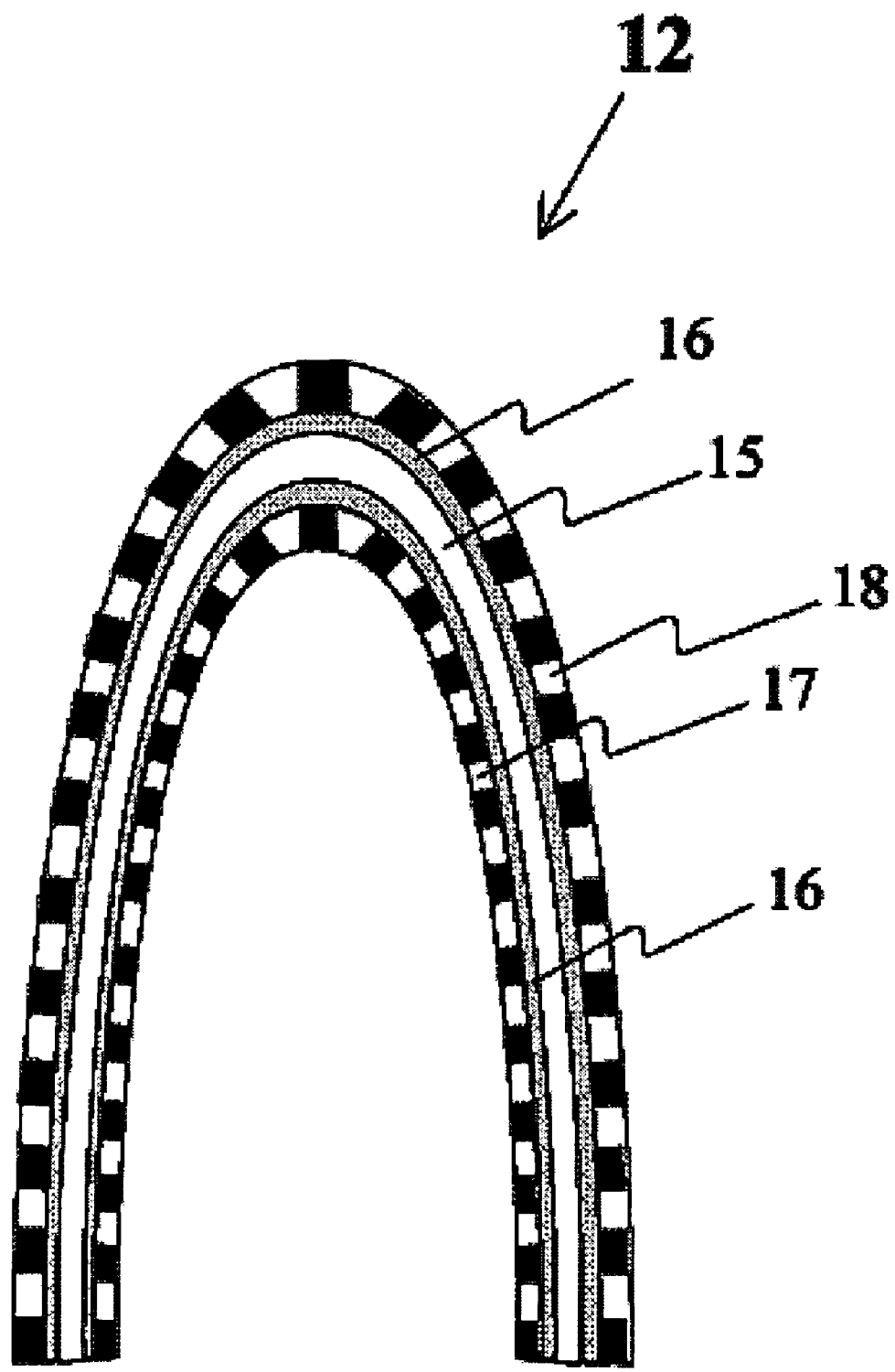
FIG. 1C illustrates a fragmentary cross-sectional view of a polymeric shell latex article supported by a cut-resistant liner bonded to the outside of the polymeric shell by an adhesive layer and a moisture-management liner bonded to the interior surface of the polymeric shell by an adhesive layer in accordance with the present invention.

Referring to FIG. 1C, there is shown a fragmentary portion of a supported polymeric shell 12, i.e., a finger portion of a cut-resistant, moisture-absorbing glove, comprising a polymeric shell 15, a moisture-absorbing, skin-contacting liner 17, adhesive layers 16, and a cut-resistant liner 18. During processing, the polymeric shell is turned inside-out with the adhesive layer over the outer surface. The moisture-absorbing liner is applied over the adhesive layer and heated to melt the adhesive layer, thereby creating a bond between the polymeric shell and the moisture-absorbing liner. Subsequently, the polymeric shell is turned inside out, a non-tacky adhesive layer is applied, and then the cut-resistant liner is applied and heated to melt the adhesive layer, thereby creating a bond between the polymeric shell and the cut-resistant liner. The adhesive-melting step for the moisture-absorbing liner and the cut-resistant liner can be combined. As described above for the moisture-absorbing glove, the bond between the polymeric shell, the adhesive layer, and the liners prevents the excessive stretching of the polymeric shell and, therefore, delamination at the interface between the polymeric shell and the adhesive layer. In practice, after the bond between the cut-resistant liner and the polymeric shell is achieved, the external surface of the cut-resistant liner can be coated with a protective, flexible, polymeric layer, such as polyurethane latex, so as to provide improved product appearance and to protect the cut-resistant fibers from damage.

Figure 1D:
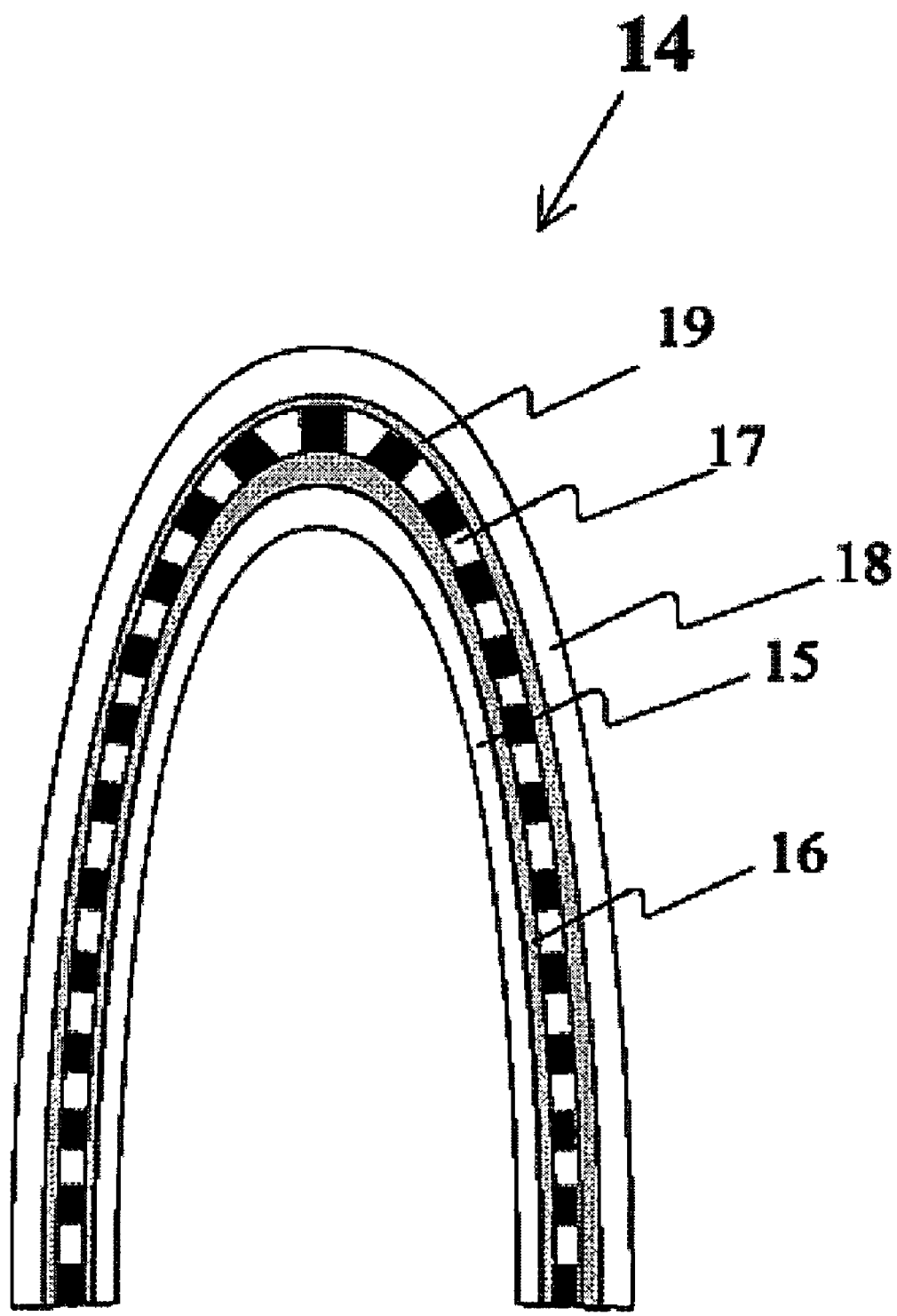
FIG. 1D illustrates a fragmentary cross-sectional view of a polymeric shell latex article with two polymeric shells supported by a cut-resistant liner bonded there between by adhesive layers in accordance with the present invention.

Referring to FIG. 1D, there is shown a fragmentary portion of a supported polymeric shell 14, i.e., a finger portion of a cut-resistant glove, comprising a polymeric shells 15 and 18, a cut-resistant liner 17, and adhesive layers 16 and 19. During processing, the polymeric shell is coated with a non-tacky adhesive layer over the outer surface, and the liner is applied over the adhesive layer. A second polymeric shell is turned inside out, coated with a non-tacky adhesive layer, turned inside out again, and slipped over the liner. Alternatively, the liner can be coated with the non-tacky adhesive layers and slipped over the first polymeric shell. Then, the second polymeric shell can be slipped over the liner. The bond between the polymeric shells and liner by way of the adhesive layers prevents the excessive stretching of the shells and delamination at the interfaces between the shells and the liner.

Figure 2A:
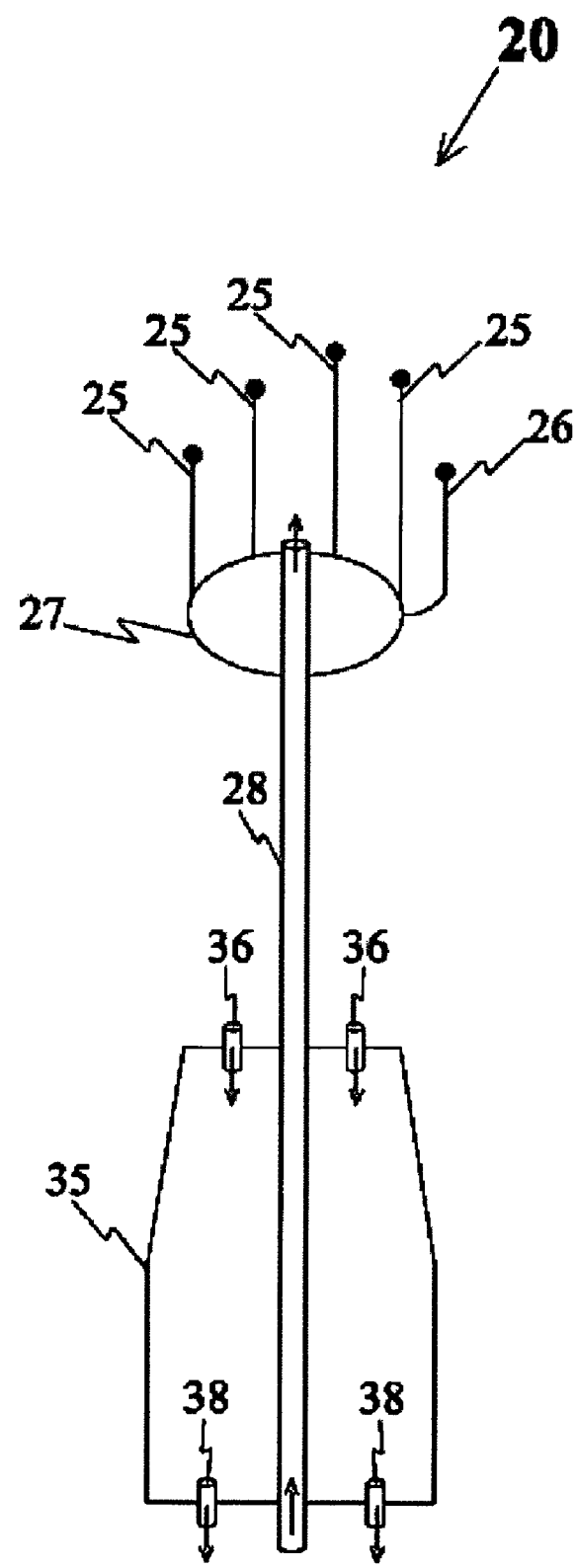
FIG. 2A illustrates a front elevational view of a skeletal mandrel for attaching a polymeric shell and means for inflating the polymeric shell in accordance with the method of the present invention.

Referring to FIG. 2A, there is shown a skeletal support 20 for a polymeric shell. The skeletal support can be used to apply the adhesive layer over the polymeric shell or to dress an adhesive-coated component. The supports aid in creating a bond between the shell and the liner upon melting of the adhesive layer. Means are provided to inflate the polymeric shell so that the adhesive-coated polymeric shell contacts the liner during the melting of the adhesive layer. A skeletal support for an article in the shape of a glove comprises finger supports 25 and a thumb support 26 as shown in FIG. 2A. The finger and thumb supports are attached to a wire member 27, which is attached to a tubular member 28. The tubular member 28 is welded to a conical chamber 35 and exits the chamber as shown. The conical chamber 35 has air vent openings at 36 and 38 designed to vent the inflating air. The arrows show the airflow within the skeletal support. Compressed air is connected to the tubular element 28 at the bottom of the conical chamber 35 and provides air pressure at the finger support 25 and thumb support 26.

Figure 2B:
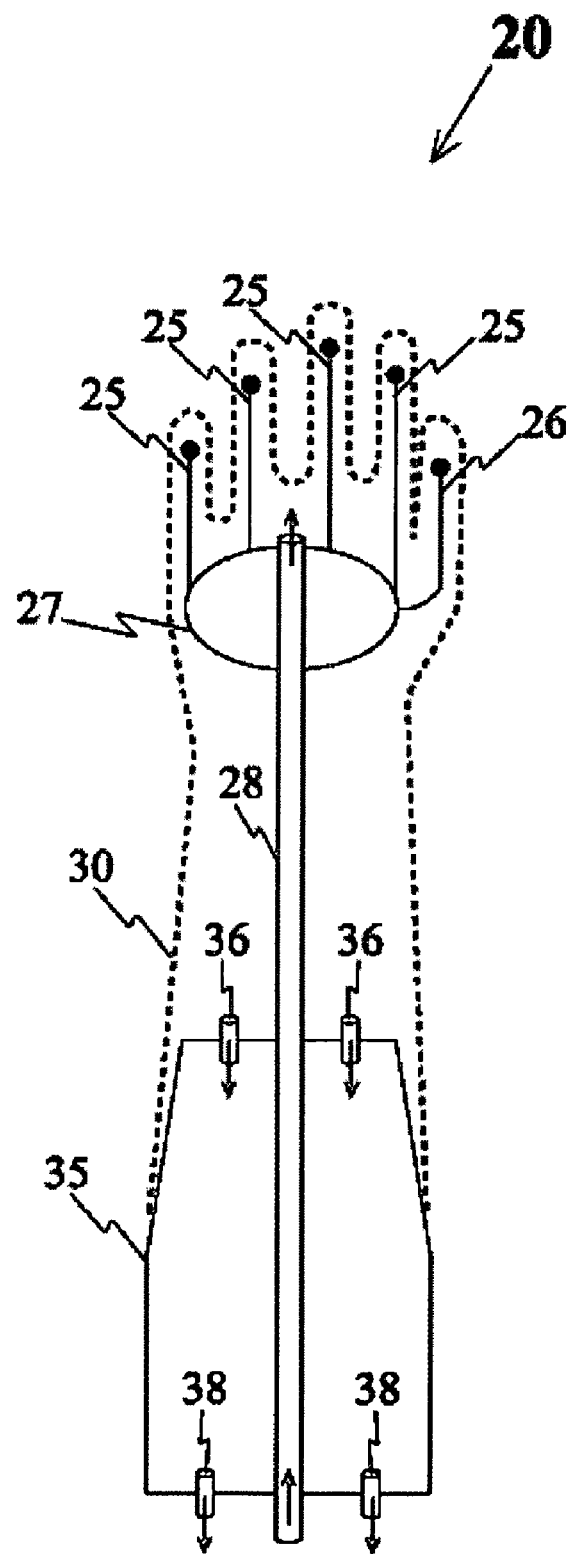
FIG. 2B illustrates an assembly of the skeletal mandrel of FIG. 2A including a polymeric shell and a liner with an adhesive layer there between depicted in broken-line.

Referring to FIG. 2B, there is shown a front elevational view of a skeletal support 20 with an article in the shape of a glove shown in dotted lines dressed over the skeletal support. The finger supports 25 are inserted into corresponding glove fingers and the thumb support 26 is inserted into the glove thumb. The glove covers the conical chamber 35. It can be clamped to prevent the displacement of the glove shell when air pressure is applied. The clamping means are not shown. The shell can be coated with a thin adhesive layer, which is solid at ambient temperature. The liner is slipped over the adhesive-coated shell. Alternatively, the inner surface of the liner can be coated with the adhesive layer and slipped over the shell. Air pressure (arrows) is applied through the tube 28 welded to the conical chamber 35, and travels through the central support tube 28, exiting at the finger supports 25 and thumb support 26. The air pressure inflates the polymeric shell, and the air is exhausted through the ports 36 and 38. The pressure within the polymeric shell is minimal due to the venting action, and the polymeric shell is pressed against the liner with the adhesive layer there between. The assembly is then taken to the heating station to melt the adhesive layer.

Figure 2C:
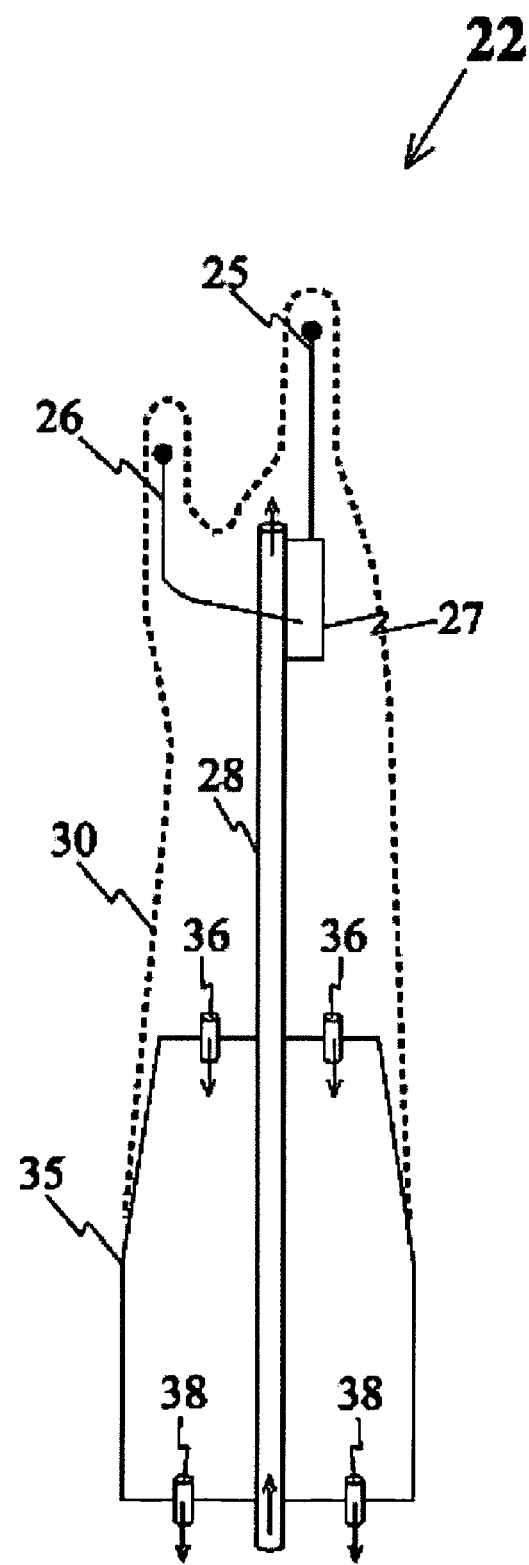
FIG. 2C illustrates a side elevational view of the assembly of FIG. 2B.

Referring to FIG. 2C, there is shown a side elevational view 22 of an article in the shape of a glove shown in dotted lines 30 dressed over a skeletal support. The finger supports 25 are inserted into corresponding glove fingers, and the thumb support 26 is inserted into the corresponding glove thumb. The glove covers the conical chamber 35. It can be clamped to prevent the displacement of the polymeric glove shell when air pressure is applied. The clamping means are not shown. The polymeric shell can be coated with a thin adhesive layer, which is solid at ambient temperature. The liner is easily slipped over the adhesive-coated polymeric glove shell. Alternatively, the liner can be coated with the adhesive layer and slipped over the shell. Air pressure (arrows) is applied through the tube 28 welded to the conical chamber 35 and travels through the central support tube 28, exiting at the finger supports 25 and the thumb support 26. The air pressure inflates the shell, and the air is exhausted through ports 36 and 38. The pressure within the shell is minimal, due to the venting action, and the polymeric shell is pressed against the liner, with the adhesive layer there between. The assembly is then taken to the heating station to melt the adhesive layer.

The present invention provides a supported polymeric shell, which is substantially free from defects, such as pinholes or cracks, and which provides excellent chemical resistance. Since the liner supports the polymeric shell, it cannot be stretched to degrade the adhesive layer bonding the polymeric shell to the liner. The liner, such as one made from cotton and/or rayon, can contact the skin of the user and provide excellent moisture absorption, i.e., sweat management. Alternatively, the liner, such as one made from steel wire, Kevlar™, and/or Spectra™, can be on the outside of the shell or within the shell and provide cut-resistance. The inner surface of such a shell can still comprise a moisture-absorbing liner.

The polymeric shell can be appropriately shaped for a number of applications including, but not limited to, a glove, a gauntlet, a boot, an apron and other industrial protective articles, which require chemical resistance and mechanical integrity. The chemical resistance is provided by a high quality, pinhole-free, polymeric shell, and the strength properties are provided by the liner, which is permanently attached to the polymeric shell by an adhesive layer.

EXAMPLES

The following examples serve to illustrate the present invention and are not intended to limit its scope in any way.

Example 1

A nitrile polymeric shell was prepared by conventional dipping in an aqueous latex emulsion, using a coagulant to gel the nitrile latex, and curing to crosslink the polymer. A layer of thermoplastic polyurethane adhesive was hot-melt sprayed on the nitrile polymeric shell by spraying approximately 3 grams of the adhesive for a pair of gloves. A conventional knitting process prepared a cotton liner. The liner was placed on the adhesive-coated polymeric shell and heated to 125° C. using an infrared heat source. The assembly was cooled. The liner was permanently bonded to the supporting knitted liner. The supported nitrile polymeric shell was kept in ambient moist air to cure and cross-link the thermoplastic polyurethane adhesive.

Example 2

A strip from Example 1 was cut and evaluated for bond strength. The bond strength was measured using the test procedure BS EN ISO 2411:200, "Rubber- or Plastics-Coated Fabrics. Determination of Coating Adhesive," (B.S.I. Chiswick, High Road, London, United Kingdom). The peel strength was measured by literally peeling the liner apart from the polymeric shell. Each free end of the joined polymeric shell and liner was held in the jaws of a tensiometer, and opposing forces were applied to peel the two apart. The units of measurement are stated in Newton force (N) per 50 mm of peel width, that is, N/50 mm width of peel line. The article was characterized by a minimum peel strength of 35 N/50 mm width of peel line. More often, the peel strength exceeded 63 N/50 mm in width, and the peeled sections were characterized by fragmented liner still attached to the polymeric shell, indicating that the liner provided support to the polymeric shell until the supporting liner fragmented.

The subject invention provides a supported polymeric shell characterized by a combination of properties including:

a) a pinhole- or defect-free polymeric shell;

b) the polymeric shell bonded to a liner using a thermoplastic adhesive layer placed between the polymeric shell and the liner;

c) the adhesive layer being substantially tack-free at ambient temperature;

d) the adhesive layer melting at a temperature below degradation temperature of the polymeric shell or the liner; and e) the bond between the polymeric shell and the liner achieved by heating to melt the adhesive layer placed between a liner and a polymeric shell and cooling the heated supported polymeric shell, wherein the bonded liner limits the stretchability of the polymeric shell, thereby preventing the separation of the adhesive layer polymeric shell interface.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. An article comprising:
   a) at least one cured, liquid-impervious polymeric shell substantially free from defects and in the shape of a glove;
   b) at least one liner; and
   c) a non-tacky, thermoplastic adhesive layer placed between the at least one shell and the at least one liner;
   wherein the adhesive layer is melted and solidified to create a non-tacky bond between the at least one shell and the at least one liner, and
   whereby the liner supports and limits stretchability of the shell, thereby preventing adhesive delamination between the adhesive layer and either of the at least one shell, the at least one liner, or both.

2. The article of claim 1, wherein the liner comprises a woven textile fabric.

3. The article of claim 1, wherein the liner comprises a knitted textile fabric.

4. The article of claim 1, wherein the liner comprises a fabric fabricated from cotton, rayon, polyester, polypropylene, Kevlar™, Spectra™, steel wire, or a combination thereof.

5. The article of claim 1, wherein the adhesive layer comprises a polymer selected from the group consisting of low molecular weight polyethylene, polyester, ethyl vinyl acetate, ethylene 2-ethyl hexyl acrylate polymer, and polyurethane, and has a melting point of less than about 140°C.

6. The article of claim 1, wherein the adhesive layer comprises a moisture-cure, cross-linking polyurethane.

7. The article of claim 1, wherein the adhesive is applied in the range of about 0.001-0.01 gram/cm$^2$.

8. The article of claim 1, wherein the liner has stretch ability in the range of about 0.5-20%.

9. The article of claim 1, wherein the article is a glove or a gauntlet.

10. The article of claim 1, wherein the liner comprises a cut-resistant liner and the article further comprises a second adhesive layer, and a moisture-absorbing liner, wherein the second adhesive layer creates a bond between the moisture-absorbing liner and the shell.

11. The article of claim 1, wherein the liner comprises a cut-resistant liner.

12. The article of claim 1, wherein the adhesive layer has a greater stretch ability than the at least one liner, and the at least one shell has a stretch ability that is greater than or equal to the stretch ability of the adhesive layer.

13. The article of claim 1, wherein the shell comprises a natural latex composition and/or a synthetic latex composition.

14. The article of claim 13, wherein the synthetic latex composition is nitrile latex.

15. The article of claim 1, wherein the article comprises a skin-contacting surface, the liner is on the skin-contacting surface, and the liner absorbs moisture.

16. The articles of claim 15, wherein the liner comprises cotton and/or rayon.

17. The article of claim 1, wherein the article comprises a non-skin-contacting surface, the liner is on the non-skin-contacting surface, and the liner is cut-resistant.

18. The article of claim 17, wherein the liner comprises steel wire, Kevlar™, Spectra™, or a combination thereof and is optionally encapsulated with a flexible, polymeric coating.

* * * * *